(12) United States Patent
Domici, Jr. et al.

(10) Patent No.: US 6,475,194 B2
(45) Date of Patent: Nov. 5, 2002

(54) SAFETY SYRINGE (75) Inventors: John K. Domici, Jr., Flemington, NJ (US); Mario Verdi, Randolph, NJ (US); Francisco Garza, El Paso, TX (US)

(73) Assignee: Gem Plastics, Inc., Hillsborough, NJ (US)

( * ) Notice: Subject to any disclaimer, the term of this patent is extended or adjusted under 35 U.S.C. 154(b) by 0 days.

(21) Appl. No.: 09/824,569

(22) Filed: Apr. 3, 2001

(65) Prior Publication Data

US 2001/0037088 A1 Nov. 1, 2001

Related U.S. Application Data (60) Provisional application No. 60/194,630, filed on Apr. 5, 2000.

(51) Int. Cl.[7] ................................................ A61M 5/32
(52) U.S. Cl. .................... 604/198; 604/187; 604/197; 604/192; 604/218; 604/235
(58) Field of Search .................... 604/187, 181, 604/197, 198, 218, 232, 235, 110, 192

(56) References Cited

U.S. PATENT DOCUMENTS

| | | |
|---|---|---|
| 4,723,943 A | 2/1988 | Spencer |
| 4,801,295 A | 1/1989 | Spencer |
| 4,840,185 A | 6/1989 | Hernandez |
| 4,915,702 A | 4/1990 | Haber |
| 4,994,045 A | 2/1991 | Ranford |
| RE33,585 E | 5/1991 | Haber et al. |
| 5,019,051 A | 5/1991 | Hake |
| 5,057,079 A | 10/1991 | Tiemann et al. |
| 5,067,490 A | 11/1991 | Haber |
| 5,137,521 A | 8/1992 | Wilkins |
| 5,201,708 A * | 4/1993 | Martin ........................ 604/110 |
| 5,219,333 A | 6/1993 | Sagstetter et al. |
| 5,279,584 A | 1/1994 | Dillard, III et al. |
| 5,312,370 A | 5/1994 | Talonn et al. |
| 5,328,473 A | 7/1994 | Fayngold et al. |
| 5,356,392 A | 10/1994 | Firth et al. |
| 5,385,555 A | 1/1995 | Hausser |
| 5,415,645 A | 5/1995 | Friend et al. |
| 5,433,712 A * | 7/1995 | Stiles et al. ................ 604/110 |
| 5,437,639 A | 8/1995 | Malenchek |
| 5,573,513 A | 11/1996 | Wozencroft |
| 5,658,254 A | 8/1997 | Reichenbach et al. |
| 5,980,494 A | 11/1999 | Malenchek et al. |
| 6,090,077 A | 7/2000 | Shaw |
| 6,319,234 B1 * | 11/2001 | Restelli et al. .............. 604/110 |
| 6,368,303 B1 * | 4/2002 | Caizza ........................ 604/110 |

* cited by examiner

Primary Examiner—Robin O. Evans (57) ABSTRACT

An improved safety syringe device includes a shield from which a vacuum needle extends and retracts, a vial that is telescopically received within a cavity of the shield and that attaches to the vacuum needle at its distal end, and a ring rotatably connected around a portion of the vial near its distal end. The vial includes a protrusion that engages with a tab on the ring to move the tab within a channel defined on the interior surface of the shield cavity. The safety syringe device further includes a temporary locking feature to maintain the vial at a generally fixed position within the shield during use of the syringe.

18 Claims, 7 Drawing Sheets

SAFETY SYRINGE

CROSS-REFERENCE TO RELATED APPLICATIONS

This application claims priority from U.S. Provisional Patent Application Ser. No. 60/194,630 entitled "Improved Safety Syringe", filed Apr. 5, 2000. The disclosure of this provisional application is incorporated herein by reference in its entirety.

BACKGROUND OF THE INVENTION

1. Field of the Invention

This invention relates to an improved safety syringe device. More particularly, this invention relates to a safety syringe device having a shield and employing a tracking system for providing automatic retraction of a syringe needle within the shield after a one-time use of the device.

2. Discussion of the Related Art

Syringes that extend and retract within a shield, thereby providing protection against an inadvertent needle strike, are well known in the art. A syringe that is capable of automatically retracting a needle within a shield upon discharging fluid from the syringe is highly desirable to reduce the risk of needle exposure after the syringe has been used. Automatic retraction syringes have been offered in the art; however, an effective syringe has not been offered which permits the needle to be easily retracted into the shield when the liquid within the syringe has been completely discharged. Nor have the previous syringes been sufficiently inexpensive in production to permit their widespread adoption.

U.S. Pat. No. 5,980,494 (Malenchek et al.) discloses a safety syringe device employing an automatic retraction feature for the syringe needle. The Malenchek et al. device includes a housing having a bore extending in an axial direction from its proximal end to its distal end. A vial is disposed within the housing bore and may be axially displaced between retracted and extended positions. The vial has a fluid receiving chamber for receiving a plunger extending between its proximal and distal ends. The vial also has a needle secured to its distal end that is in fluid communication with the vial chamber, and the needle is fully retracted in the housing bore when the vial is in the retracted position. The needle extends from the bore distal end when the vial is in the extended position. A positioning means, responsive to an initial vial axial displacement, releasably locks the vial in the extended position. The positioning means permits unlocking of the vial upon a subsequent vial axial displacement and further permits automatic displacement of the vial to the retracted position after the vial is unlocked. The positioning means includes grooves and ratchet teeth defined on the interior surface of the housing bore, a ratchet member disposed on the exterior surface of the vial and a ring disposed around the vial with camming tabs that engage the ratchet teeth of the housing and the ratchet member of the vial. The syringe disclosed in the Malenchek et al. patent is not reliable in operation and is very expensive to manufacture. Moreover, the design is not suitable for low cost mass production of the device.

An improved design of a safety syringe that provides easy and reliable automatic retraction of the syringe needle into the housing after liquid is completely expelled from the vial is therefore highly desirable.

OBJECTS AND SUMMARY OF THE INVENTION

An object of the present invention is to provide an improved safety syringe that is easy to manufacture, in machining of parts as well as assembly, and reliable during use. Another object of the invention is to provide a safety syringe that is suitable for low cost mass production.

A further object of the invention is to provide a safety syringe having a temporary locking position that maintains exposure of the needle outside of the shield during aspiration of fluid into its vial, and automatically retracts the needle to a locked position within the shield after fluid is completely discharged from the vial.

The aforesaid objects are achieved individually and/or in combination, and it is not intended that the present invention be construed as requiring two or more of the objects to be combined unless expressly required by the claims attached hereto.

In accordance with the present invention, an improved safety syringe includes a vial having a distal end configured for attachment with a vacuum needle, wherein the vial has at least one first protrusion and at least one second protrusion extending from an exterior surface of the vial. The second protrusion is circumferentially spaced a selected distance from the first protrusion along the exterior surface of the vial. The vial has a cavity defined between its proximal and distal ends, and the vial cavity is configured to telescopically receive a plunger at an aperture defined at the vial distal end. A ring is rotatably and slidably secured around the vial between the vial distal end and the protrusions. The ring has at least one tab projecting from an exterior surface of the ring, and the tab includes an engaging surface configured to engage with complimentary engaging surfaces on each of the protrusions.

A shield telescopically receives the vial and ring at an aperture defined at its proximal end. The shield also has an aperture defined at its distal end and a cavity defined between the proximal and distal ends and in communication with both apertures. The aperture at the shield distal end permits the vacuum needle, when attached to the vial, to extend from or retract into the shield cavity. An interior surface of the shield defines at least one channel configured to receive the tab of the ring. A resilient member is further placed within the shield cavity to bias the ring and vial toward the shield proximal end.

A first ridge and a second ridge are disposed on a raised portion of the shield interior surface adjacent the channel. The ridges face the shield distal end with a valley defined therebetween. The valley is configured to receive and hold the tab on the ring in a temporary locked position during aspiration of fluid into the vial. In addition to its axial bias, the resilient member may also rotationally bias the ring in a direction from the first ridge to the second ridge of the channel.

The above and still further objects, features and advantages of the present invention will become apparent upon consideration of the following detailed description of specific embodiments thereof, particularly when taken in conjunction with the accompanying drawings wherein like reference numerals in the various figures are utilized to designate like components.

BRIEF DESCRIPTION OF THE DRAWINGS

FIG. 2a is a cross-sectional view of the shield taken along lines 2a—2a of FIG. 2.

FIG. 2b is an enlarged view of a portion of the shield of FIG. 2a.

FIG. 2c is a view in longitudinal cross-section of the distal end portion of the shield of FIG. 2.

FIG. 2d is a enlarged view in cross-section of a portion of the shield taken along lines 2d—2d in FIG. 2c.

DETAILED DESCRIPTION OF THE PREFERRED EMBODIMENTS

Figure 1:
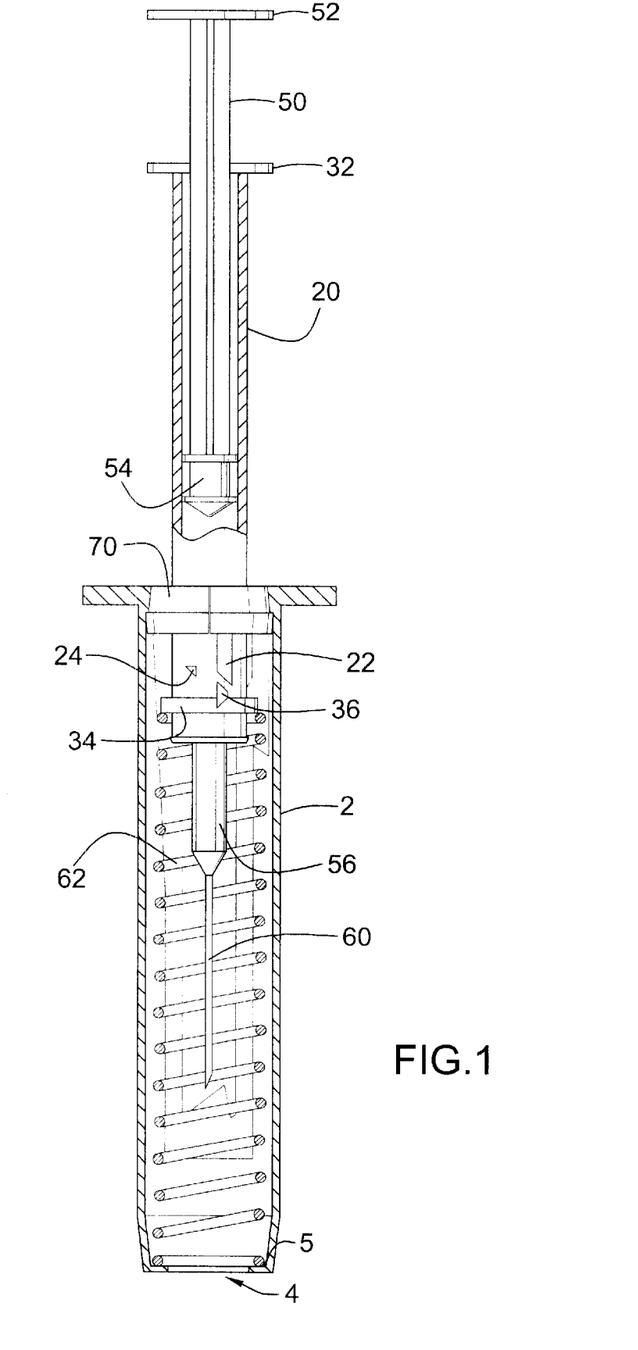
FIG. 1 is a longitudinal view in cross-section of a first embodiment of the safety syringe according to the invention wherein the syringe is in a first needle retracted position.
Figure 3:
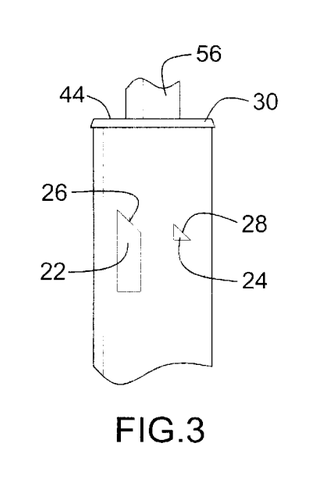
FIG. 3 is a broken longitudinal view in elevation of a portion of the vial of FIG. 1 at its distal end.
Figure 4:
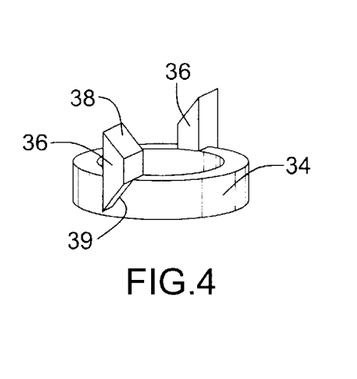
FIG. 4 is a perspective view of the ring of FIG. 1.

An exemplary embodiment of the safety syringe of the present invention is illustrated in FIG. 1, wherein the needle is in a first retracted position within the shield and ready for use. Individual components of the device are further presented in an exploded view of the device depicted in FIG. 2 as well as in FIGS. 3 and 4. All of the components may be constructed utilizing any conventional or other material sufficient for facilitating operation of the syringe. Unless specified otherwise, all of the syringe components are preferably constructed of a clear thermoplastic material such as polypropylene.

Shield 2 is typically cylindrical and includes an internal cavity extending axially between its proximal end 6 and distal end 4. Each end of the shield includes an aperture in communication with the shield cavity, wherein the aperture at the shield distal end is typically smaller in diameter than the aperture at the shield proximal end and is of an appropriate size to facilitate passage of vacuum needle 60 into and out of the shield cavity at the shield distal end. Shield proximal end 6 includes an end wall surface extending radially outward from the shield exterior surface to define an annular flange 7, and shield distal end 4 includes an end wall surface extending radially inward from the shield exterior surface to define a supporting ledge 5 within the shield cavity. The shield cavity and aperture at shield proximal end 6 are of an appropriate size to telescopically receive and facilitate axial movement of vial 20 within the shield. A pair of elongate channels 8, circumferentially spaced from each other, are defined on an interior surface of the shield within the shield cavity. The channels are also preferably symmetrically spaced from each other along the shield interior surface. Each channel 8 extends a substantial portion of the length of shield 2 and includes a first groove 10 and a second groove 12 longitudinally aligned on the shield and separated from each other by a raised portion 11 of the shield interior surface serving as barrier between the two grooves. The grooves communicate at their distal ends (i.e., near the shield distal end) via a portion of channel 8 that extends circumferentially along the shield interior surface beyond the distal end of raised portion 11. The distal end of the raised portion is defined by a jagged surface having a pointed first ridge 14 adjacent the distal end of first groove 10, a pointed second ridge 16 adjacent the distal end of second groove 12 and a generally V-shaped valley 15 formed between the ridges. Both ridges face the shield distal end 4 and provide an inclined travel path in channel 8 along the end surface of raised portion 11. Second groove 12 of each channel further includes an angled notch 18 located near the shield proximal end and defined along the outer channel wall of the groove. The angled notch faces shield distal end 4 and serves as a barrier to engage and retain an element having a complimentary angled surface and traveling along the outer channel wall toward the shield distal end in second groove 12.

Figure 2:
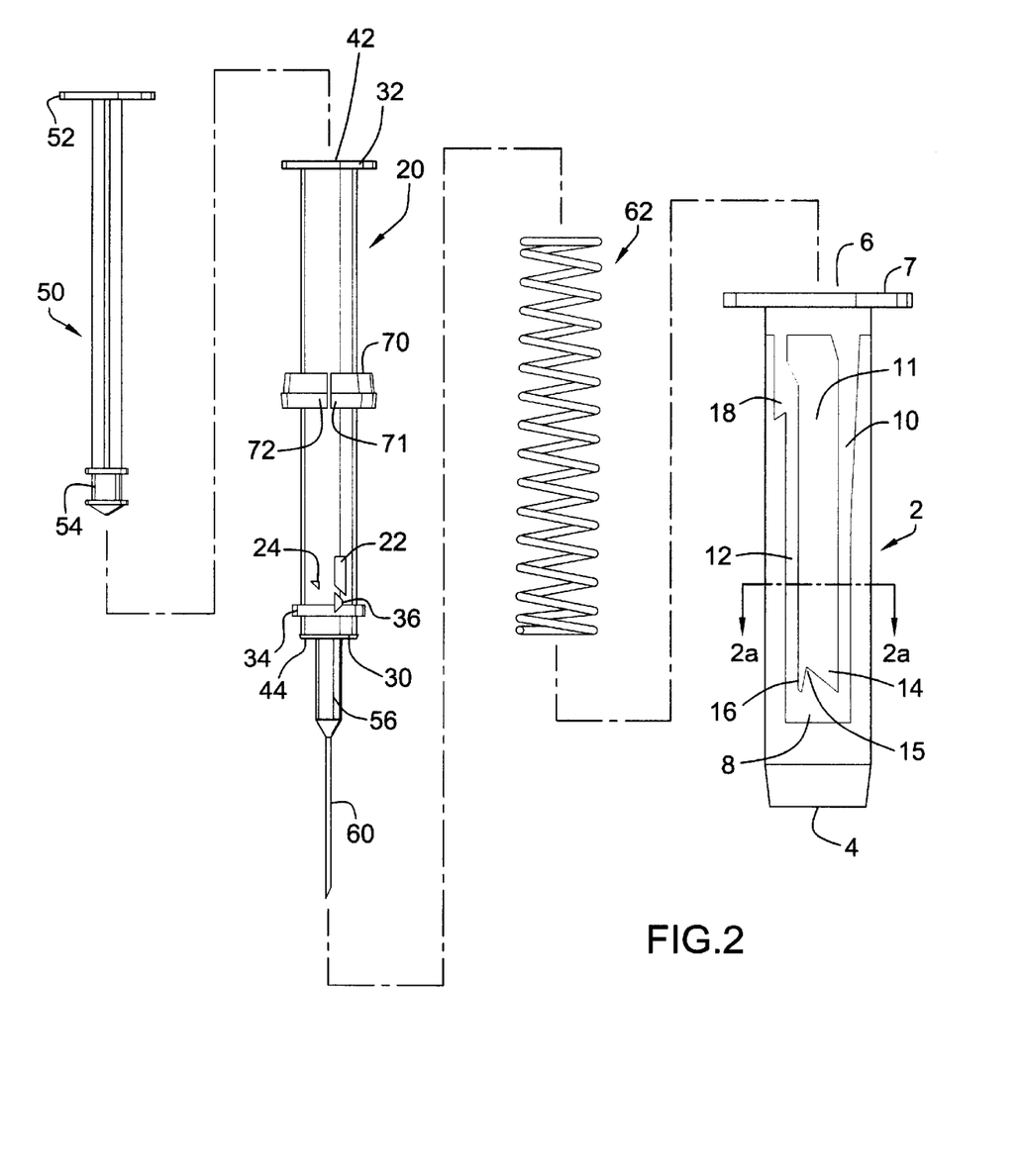
FIG. 2 is an exploded longitudinal view in elevation of the syringe of FIG. 1.
Figures 2A, 2B, 2C, 2D:
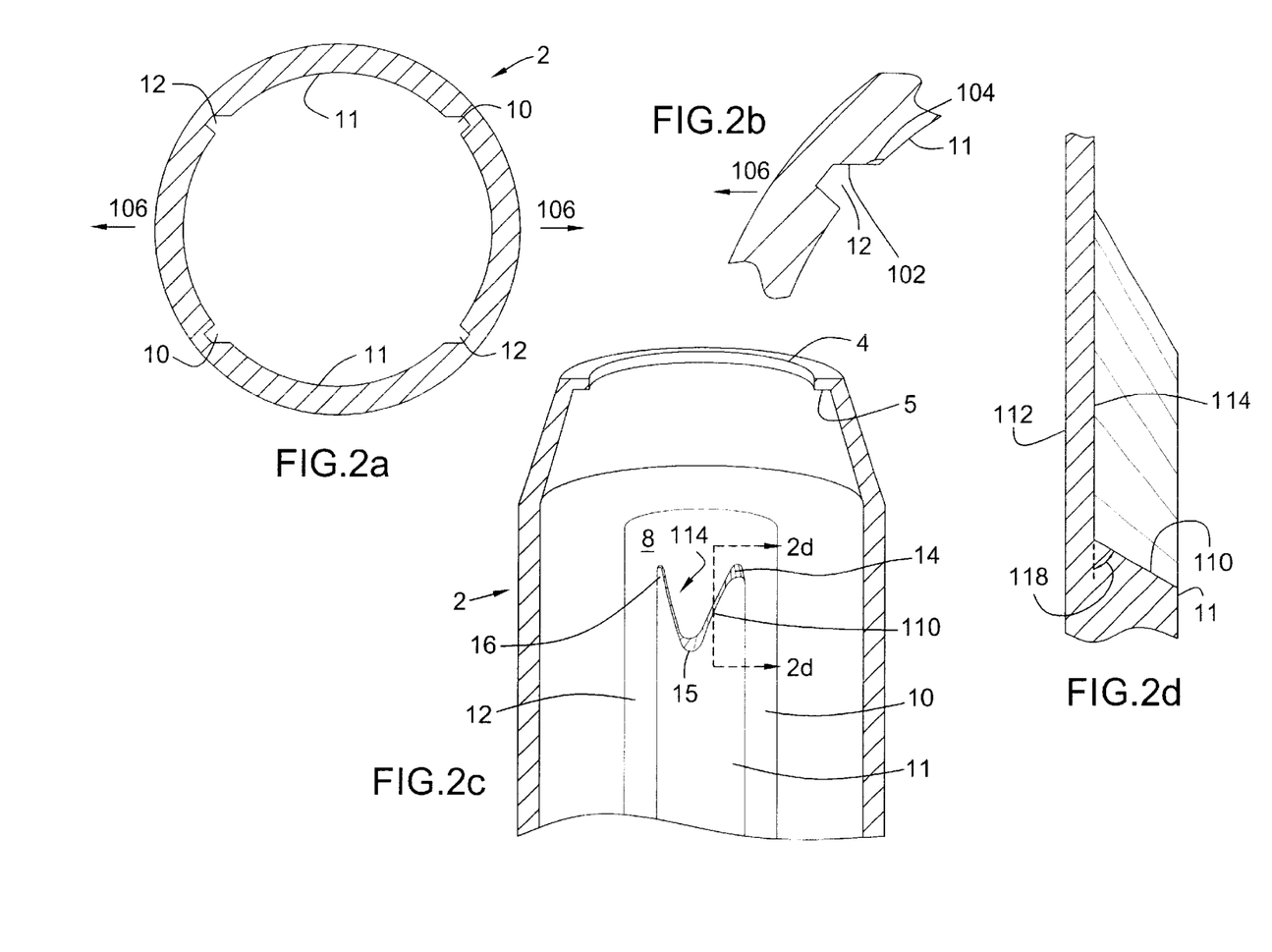

Each of the channel grooves defined in the shield interior surface preferably has at least one channel wall that is non-perpendicular to the shield interior surface to facilitate easy construction of the shield. The typical cross-sectional profile of each groove is illustrated in FIGS. 2a and 2b. FIG. 2a depicts a cross-sectional view of the shield taken along lines 2a—2a in FIG. 2, and FIG. 2b depicts an enlarged view of one of the grooves illustrated in FIG. 2a. Each groove 10, 12 is defined by channel walls extending into the interior surface of the shield. At least one of the channel walls for each groove typically extends from an adjacent shield interior surface such that the angle defined between the channel wall and the adjacent shield interior surface is greater than 90°. For example, as illustrated in FIG. 2b, an angle 104, which is greater than 90°, is formed at the junction of a channel wall 102 of second groove 12 and interior surface raised portion 11. The other channel wall of second groove 12 extends in a generally perpendicular manner from the interior surface of the shield, thus rendering the cross-sectional geometric profile of the groove generally trapezoidal. The other grooves of the shield have generally similar profiles.

Angling at least one channel wall from the shield interior surface in the manner described above for each groove facilitates easy removal of the shield from a forming die after it is formed (e.g., in a molding or drawing process) and reduces the potential for shearing of one or more channel walls in the grooves when the shield is removed from the forming die. For example, a shield is typically removed from a forming die after it is formed by applying drawing forces in substantially equal and opposite directions to the shield to radially stretch the shield. The shield interior diameter is increased to an appropriate size to allow it to slide from the exterior surface of the die. Arrows 106 in FIGS. 2a and 2b are representative of two equal and opposite drawing forces applied to radially stretch the shield. The angle of the channel walls for each groove and the direction in which the drawing forces are applied to the shield are typically selected so that each angled channel wall is parallel to a drawing force applied to the shield. By providing angled channel walls and applying drawing forces to the shield in this manner, each angled channel wall slides along a complimentary surface of the die rather than scraping a die edge as the shield is radially stretched away from the die.

The distal end of the shield interior surface raised portion 11 between ridges 14, 16 is preferably defined by a spline, rotating surface as illustrated in FIGS. 2c and 2d and described below. FIG. 2c depicts a longitudinal cross-sectional, view of the shield at its distal end 4, and FIG. 2d depicts an enlarged view of a further cross-sectional portion of the shield taken along lines 2d—2d of FIG. 2c. Specifically, the distal end spline surface 110 of raised portion 11 forms a semi-helical path as it extends from ridge 14 to valley 15 and another semi-helical path as it extends from valley 15 to ridge 16. The contour of spline surface 110 is controlled by varying the angle at which it extends from an adjacent channel surface 114 of channel 8 as the spline surface extends between the two ridges. A transition angle 118 is defined as the angle at which spline surface 10 extends or ramps from channel surface 114. Transition angle 118 preferably varies between about 30° and about 60° as spline surface 110 extends between each ridge 14, 16 and valley 15, resulting in the semi-helical path of the spline surface as depicted in FIGS. 2c and 2d. Preferably, the transition angle is about 30° at the ridges and the valley and about 60° at the midpoint of the spline surface between each ridge and valley. Providing a spline, rotating surface at the distal end of the shield interior raised portion minimizes the likelihood of shearing of the shield between the ridges during removal of the shield from a forming die.

Vial 20 is typically cylindrical in shape. However, the vial may have any geometric configuration that allows it to be axially displaced within the shield cavity. The vial has apertures at its proximal and distal ends and an internal cavity extending axially between and in communication with the apertures. A flange 32 extends radially from the vial exterior surface at the vial proximal end 42 to provide a gripping surface for which a user may axially move the vial within the shield cavity. The aperture at vial distal end 44 is configured for attachment with a needle assembly 56 in any conventional or other manner (e.g., by frictional engagement, threaded engagement, etc.). The vial cavity is appropriately dimensioned to telescopically receive an elongated plunger 50 via the aperture at vial proximal end 42. The plunger typically has a rubber stopper portion 54 at its distal end that is dimensioned to frictionally engage and provide a seal against the internal walls within the vial cavity. Thus, pulling plunger 50 in an axial direction from the aperture at vial proximal end 42 facilitates aspiration of fluid from vacuum needle 60 into needle assembly 56, through the aperture at vial distal end 44 and into the vial cavity. Plunger 50 also has a flange 52 extending radially from its exterior surface at its proximal end to provide a gripping surface for which a user may axially displace the plunger within the vial cavity.

A pair of circumferentially spaced first protrusions 22 protrude from the exterior surface of vial 20 near its distal end 44. The first protrusions are typically spaced symmetrically from each other along the vial exterior surface. Another pair of second protrusions 24 protrude from the vial exterior surface, and each second protrusion 24 is circumferentially spaced a selected distance from a respective first protrusion 22. Each protrusion 22, 24 has an engaging surface 26, 28 (FIG. 3) generally facing the receptacle distal end 44 and angled to engage in a camming relationship with another complimentary angled surface. Each of the protrusions are appropriately dimensioned and aligned on the vial so as to facilitate proper engagement with tabs 36 on a ring 34 and operation of the syringe as described below. The vial further includes a flange 30 extending radially from the exterior surface of the vial at its distal end 44.

Ring 34 is secured around vial 20 and has an inner diameter slightly larger than the outer diameter of vial 20 to allow both rotational and axial movement of the ring with respect to the vial. Ring 34 is located between the protrusions and the flange of the vial. Protrusions 22 and flange 30 provide boundaries which limit the axial movement of the ring in either direction along the vial. A pair of tabs 36 (FIG. 4) protrude from the exterior surface of ring 34 and are circumferentially spaced from each other along the ring a selected distance so that, upon placement of the ring around the vial, the pair of tabs may be aligned with each pair of protrusions on the vial. Each tab is disposed longitudinally along the exterior surface of the ring and typically extends beyond the ring proximal end. The end of each tab extending beyond the ring proximal end includes an engaging surface 38 that is angled in a generally complimentary manner to the engaging surfaces 26, 28 of the protrusions as well as the angle of incline of each spline surface 110 extending between a respective first ridge 14 and valley 15. The end of each tab located at the ring distal end includes an engaging surface 39 that is angled in a complimentary manner to the angled notch 18 of each second groove 12.

A resilient member 62 is provided within the shield to resiliently bias the vial and ring in an axial direction toward the proximal end of the shield. The resilient member is typically a cylindrical compression coil spring that is appropriately dimensioned to fit securely within the shield cavity and allow the vial distal end, needle assembly and needle to pass through its coils without any contact or resistance. The resilient member may alternatively be a leaf spring or any other resilient material capable of resiliently biasing the vial and ring toward the shield proximal end and facilitating operation of the syringe as described below. The resilient member is typically made of metal (e.g., steel) and is typically designed such that the force applied by the spring to the ring and vial, as described in greater detail below, is about 0.4 lbs. The amount of force required to fully compress the resilient member during use of the syringe is typically in the range of 2.4 to 2.7 lbs.

Figure 5A:
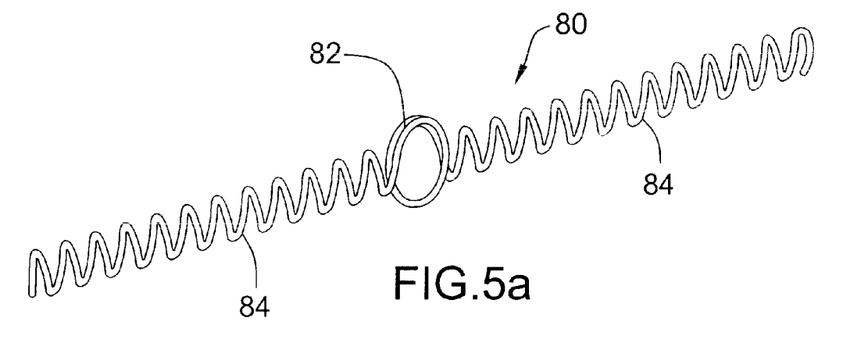
FIG. 5a is a perspective view of an alternative embodiment for the resilient member utilized in the syringe of FIG. 1, wherein the resilient member is in a substantially flat position.
Figure 5B:
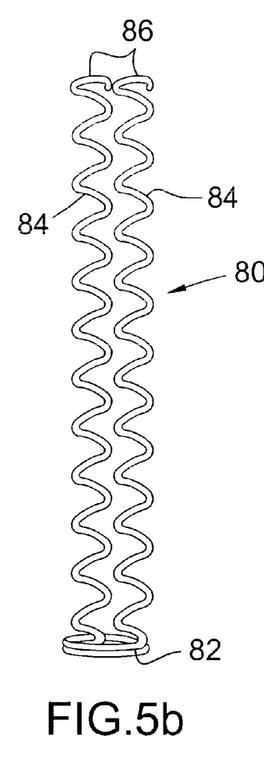
FIG. 5b is a perspective view of the resilient member of FIG. 5a, wherein the resilient member is in a bent configuration and ready for use with the syringe of FIG. 1.

An alternative embodiment for the resilient member described above is illustrated in FIGS. 5a and 5b. Resilient member 82 includes a toroidal or ring section 82 with a pair of generally linear helical members 84 extending from the ring section substantially 180° from each other along the circumference of the ring section. The resilient member is in a substantially flat and unbent position in FIG. 5a, wherein the helical members are generally coplanar with the ring section. The resilient member may be easily packaged in the unbent position with other similarly shaped resilient members in order to simplify shipment of a plurality of resilient members and mass production of the syringe device. Additionally, the unbent configuration of the resilient member virtually eliminates the potential for entanglement between two or more packaged resilient members, thus alleviating a problem that is all too common with typical coil springs. The configuration of resilient member 80 is easily modified to render it capable for use with the syringe by bending a portion of each helical member 84 near their attachment to ring section 82 approximately 90° so that the helical members are generally parallel to each other and lie in a plane generally perpendicular to the plane in which the ring section lies as illustrated in FIG. 5b. The helical members have the same general length and can be compressed in a substantially similar manner as resilient member 62. Each helical member 84 has a substantially flat end portion 86 that provides a contact surface for applying a compressive force to the resilient member. The helical members are further separated from each other in the bent configuration a distance nearly equal to the diameter of ring section 82. In the bent configuration, the resilient member is appropriately dimensioned to fit securely within the cavity of the shield while allowing the vial distal end, needle assembly and needle to pass through the ring section and space between the helical members extending from the ring section.

Manufacture and assembly of the syringe of the present invention is greatly simplified in comparison to similar syringes in the art due to the new design and reduced number of necessary components. Assembly of the syringe is accomplished by inserting resilient member 62 into the cavity of shield 2 at its proximal end 6, followed by inserting the distal end 44 of vial 20 along with ring 34 into the shield cavity. One end of the resilient member engages supporting ledge 5 at the shield distal end, and the other end of the resilient member engages the distal end of ring 34. If resilient member 80 is to be utilized in the syringe, that resilient member is inserted within the shield cavity so that ring section 82 engages the supporting ledge at the shield distal end and helical members 84 extend toward the shield proximal end. Needle 60 can be attached via needle assembly 56 to vial distal end 44 before or after the vial is placed within the shield. For example, the needle and needle assembly may be affixed to the vial distal end prior to insertion of the vial into the shield. The needle and needle assembly would simply extend within the space between the coils of the resilient member once the vial distal end is inserted into the shield cavity. Plunger 50 can also be placed within the cavity of the vial at its proximal end 42 at any time during the assembly process.

Ring 34 can be attached to vial 20 between protrusions 22, 24 and flange 30 in any conventional manner (e.g., by bonding two open ends of the ring together after connecting the ring to the vial). Ring 34 is connected to vial 20 so that engaging surfaces 38 of the tabs face engaging surfaces 26, 28 of the protrusions, and vial 20 and ring 34 are loaded into the shield with each first protrusion 22 engaging a corresponding tab 36 at their engaging surfaces 26, 38. Additionally, the first protrusions and tabs are aligned with corresponding first grooves 10 in channels 8. Each first groove 10 is appropriately dimensioned to receive and provide a travel path for a corresponding tab 36 and first protrusion 22 from the shield proximal end to a corresponding first ridge 14 at the distal end of first groove 10. Each second groove 12 is also appropriately dimensioned to receive and provide a travel path toward shield proximal end 6 for a corresponding tab 36. Furthermore, the portion of each channel 8 extending beyond the distal end of raised portion 11 is appropriately dimensioned to allow a corresponding tab 36 to traverse a corresponding first ridge 14 and subsequently travel toward and traverse a corresponding second ridge 16.

The vial is typically secured within the shield cavity utilizing a retaining guide bushing 70. The guide bushing eliminates the need for providing a cumbersome and costly manufacturing step of welding a cap portion or some similar sealing structure to the shield proximal end after insertion of the vial within the shield. The guide bushing is preferably constructed of an acetal resin material and is sufficiently dimensioned to fit tightly within the aperture at the shield proximal end while providing stability for the vial during its axial movement within the shield. Bushing 70 is generally cylindrical and has two facing ends 71, 72 that are separated by a slit extending longitudinally along the bushing. The facing ends of the bushing can be further separated to allow the bushing to be wrapped around the outer surface of vial 20. After appropriate insertion of resilient member 62, vial 20 and ring 34 within the cavity of shield 2, bushing 70 is wrapped around vial 20 between protrusions 22, 24 and vial proximal end 42 and subsequently inserted into the aperture at shield proximal end 6. Facing ends 71, 72 abut one another as bushing 70 slides into the shield aperture. Upon full insertion of the bushing into the aperture at the shield proximal end, assembly is complete and the bushing serves as an effective retainer to prevent removal of syringe components from the shield cavity during operation of the syringe. Preferably, bushing 70 is sufficiently sized such that its proximal end will be flush with the shield proximal end after complete insertion of the bushing into the aperture at the shield proximal end. Resilient member 62 biases ring 34 and vial 20 towards the shield proximal end 6, resulting in the proximal ends of protrusions 22 abutting the guide bushing which prevents further retraction of vial 20 and ring 34 from the aperture at shield proximal end 6. With the ring and vial biased toward the shield proximal end and the tabs of the ring disposed within the first grooves of the shield channels, the syringe is in a first retracted position (i.e., the vacuum needle is completely retracted within the shield) and ready for use as illustrated in FIG. 1.

During operation of the syringe, the needle passes from the first retracted position to an extended or ready-to-use position, wherein the ring and vial distal end are temporarily locked near the shield distal end and the needle is fully extended from the aperture at the shield distal end. After using the syringe to aspirate and expel fluids from the vial, the needle is retracted from the extended position to a final retracted position where the ring and vial distal end are locked near the shield proximal end and the needle is retracted within the shield. In the final needle retracted position, the syringe is typically incapable of extending the needle for additional use. Displacement of the vial and ring within the shield cavity to achieve the different positions for the needle is described below.

Specifically, vial 20 is axially displaced within the shield cavity toward the shield distal end by applying an appropriate force to the vial. The user of the syringe typically applies the force at plunger flange 52 and/or vial flange 32. The force acting on the vial must be sufficient to overcome the axial biasing tension applied by resilient member 62 at the distal end of ring 34. Shield 2 is held stationary (e.g., by gripping shield flange 7) to permit axial movement of vial 20 and ring 34 with respect to the shield. As resilient member 62 is compressed and vial distal end 44 is axially displaced toward shield distal end 4, each first protrusion 22 on the vial engages a corresponding tab 36 on the ring at their complimentary engaging surfaces 26, 38. The engagement of the first protrusions with the tabs forces ring 34 to move simultaneously with the vial in an axial direction toward the shield distal end, and the first protrusions and tabs move together within their corresponding first grooves 10 toward corresponding first ridges 14.

Figure 6:
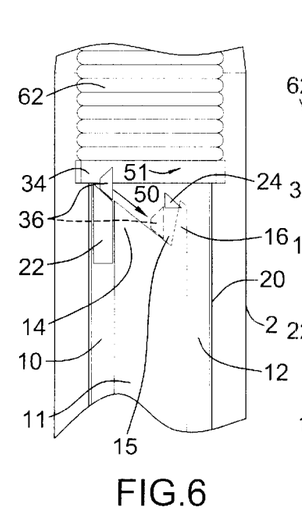
FIG. 6 is a broken longitudinal view in elevation of a portion of the syringe of FIG. 1 near its distal end wherein the vial and ring are extended within the shield.
Figure 7:
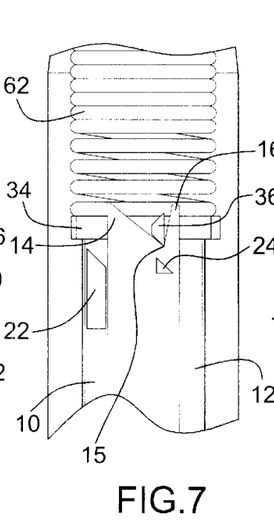
FIG. 7 is a broken longitudinal view in elevation of the portion of the syringe of FIG. 5 wherein the syringe is in a temporary locked position.
Figure 8:
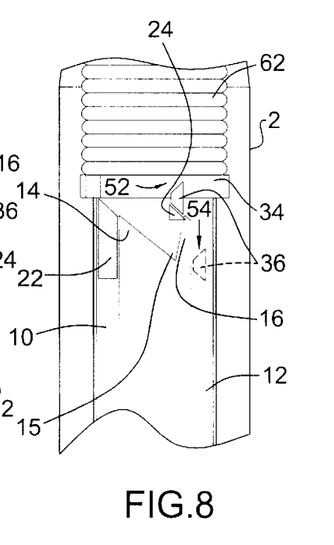
FIG. 8 is a broken longitudinal view in elevation of the portion of the syringe of FIG. 5 wherein the vial and ring are retracting within the shield.

The rotational and axial displacement of the ring within the shield during operation of the syringe is illustrated in FIGS. 6–8. Those figures depict a broken view of the syringe near its distal end. For simplification purposes, connecting portion 56 is not shown in FIG. 7 between the open portions of resilient member 62. The user of the syringe applies enough force to axially displace vial 20 and ring 34 toward the shield distal end until protrusions 22 and tabs 34 have reached the distal end of their corresponding first grooves 10 (FIG. 6). The vacuum needle is fully extended from the aperture at the shield distal end when each tab 34 extends beyond the distal end of a corresponding first groove 10 and is in position to traverse a corresponding first ridge 14 and travel within channel 8 toward a corresponding second ridge 16. Upon reaching a longitudinal position within grooves 10 that allows tabs 36 to traverse their first ridges 14 (e.g., typically the furthest point at which the vial and ring may travel axially within the shield cavity toward the shield distal end), the force applied to the vial via plunger flange 52 and/or vial flange 32 is removed. The removal of the applied force to the vial allows the axial biasing tension in resilient member 62 to act upon ring 34 and vial 20 and force them toward the shield proximal end. Simultaneously, the resilient member forces each tab 36 to slide along its corresponding first protrusion 22 via their complimentary engaging surfaces 38, 26. Such sliding or camming action forces tab 36 to traverse first ridge 14 and results in rotational displacement of ring 34 in a direction from first groove 10 toward second groove 12. In effect, the ring undergoes both an axial and rotational displacement due to the axial biasing tension of the resilient member and the camming action of the tabs. Tab 36 continues to slide along spline surface 110 from ridge 14 toward valley 15, resulting in continued rotational displacement of ring 34 toward second groove 12 and continued axial displacement of ring 34 and vial 20 toward shield proximal end 6, until reaching valley 15. The sliding movement of tab 36 between ridge 14 and valley 15 and the rotational movement of ring 34 are depicted in FIG. 6 by arrows 50, 51 and tab 36 shown in dashed lines.

When each tab 36 reaches a corresponding valley 15, the syringe is in the temporary locked position (FIG. 7), wherein the needle is fully extended from the shield and will remain in such a position until fluid is aspirated into vial 20 and subsequently expelled. The axial biasing tension of the resilient member is prevented from further acting upon the ring and vial due to the tabs being received within their corresponding valleys 15. Specifically, ring 34 is effectively locked from any axial or rotational displacement within the shield cavity due to the axial bias of resilient member 62 acting on the ring toward the shield proximal end and tabs 36 being held in valleys 15. Vial 20 is similarly locked or limited from being axially or rotationally displaced due to its flange 30 abutting the distal end of the ring and its first protrusions 22 abutting the proximal end of the ring and the sidewalls of grooves 10. If needle 60 was not previously attached to vial 20, the temporary locked position allows needle assembly 56 to be inserted into the aperture at shield distal end 4 and attached to vial distal end 44 at such time.

In the temporary locked position, needle 60 can be injected into a fluid source and plunger 50 can be withdrawn from the vial cavity until a desired amount of fluid is aspirated into the vial. The needle can be subsequently injected into a source where the fluid is to be delivered while applying an appropriate force to plunger 50 to axially displace it back into the vial cavity thereby forcing the fluid from the vial and needle. The force applied to the plunger is typically selected such that, upon complete axial displacement of the plunger and complete discharging of the liquid held within the vial cavity, the plunger transmits an appropriate force to the vial and ring to overcome the opposing biasing tension applied by resilient member 62 on the ring and vial. Alternatively, an appropriate force may be applied directly to vial 20 at any time (e.g., when fluid still remains in the vial cavity) to overcome the opposing biasing tension of the resilient member. Application of the appropriate force to the vial results in axial displacement of the vial and the ring toward shield distal end 4. Specifically, each second protrusion 24 of vial 20 engages with a corresponding tab 36 at their complimentary engaging surfaces 28, 38, thereby transmitting the applied force from the vial to the ring. Each tab 36 is removed from its corresponding valley 15 and proceeds to travel toward the shield distal end. Simultaneously the sliding or camming action between each engaging surface 28, 38 of the second protrusions and the tabs causes the ring to rotate in the direction of second ridges 16 (FIG. 8). Upon reaching a position within a corresponding channel 8 that allows each tab 36 to traverse its corresponding second ridge 16 (e.g., typically the furthest point at which the vial and ring may travel axially within the shield cavity toward the shield distal end), the applied force to the vial is removed allowing the axial biasing tension in resilient member 62 to act upon the ring and vial. The biasing tension of the resilient member forces each tab 36 to continue sliding along each corresponding second protrusion 24 via their engaging surfaces 38, 28, resulting in further rotational displacement of the ring (indicated by arrow 52 in FIG. 8) to allow tabs 36 to traverse corresponding second ridges 16 and appropriately align with corresponding second grooves 12. Once tabs 36 are appropriately aligned with corresponding second grooves 12, the biasing tension of the resilient member forces the ring and vial toward the shield proximal end. The tabs travel in their corresponding second grooves (indicated by arrow 54 and the tab 36 shown in dashed lines in FIG. 8) as the ring is axially displaced. The proximal end of the ring abuts each first protrusion on the vial, causing the vial to move with the ring. Ring 34 and vial 20 will continue to be axially displaced in the direction of shield proximal end 6 until first protrusions 22 of the vial abut bushing 70. When vial distal end 44 comes to rest near bushing 70, vial 20 and ring 34 are in the second retracted position and needle 60 is completely retracted within the shield cavity.

The vial and ring are typically permanently locked in the second retracted position due to the notch arrangement provided in second grooves 12 as well as the engaging surfaces 39 provided on tabs 36 of the ring. Notch 18 is formed within the outer wall of groove 12 near its proximal end and is configured to receive the distal end of a corresponding tab 36. As described above, engaging surface 39 of each tab 36 is appropriately angled to be complimentary to the angle provided in each notch 18. When the vial and ring are completely retracted within the shield cavity such that tabs 36 are disposed at the proximal ends of second grooves 12, the vial and ring are prevented from being axially displaced toward the shield distal end beyond the point where each tab 36 engages with a corresponding notch 18. Thus, the second retracted position effectively prevents the needle from extending from the shield and limits the operation of the syringe to a single use.

In an alternative embodiment of the invention, the syringe is modified such that the resilient member provides both an axial biasing tension and a torsional or rotational biasing tension to the ring. The rotational biasing tension can be incorporated in the design of the resilient member and/or the method in which the resilient member is loaded during assembly of the syringe. For instance, when a coil spring is utilized as described above and illustrated in FIGS. 1, 2 and 6–8, the spring may be twisted prior to loading into the syringe so as to bias the ring in a desired rotational direction within the shield. Alternatively, the resilient member may be designed such that a rotational and axial biasing tension is loaded into the spring as it is compressed.

Figure 9:
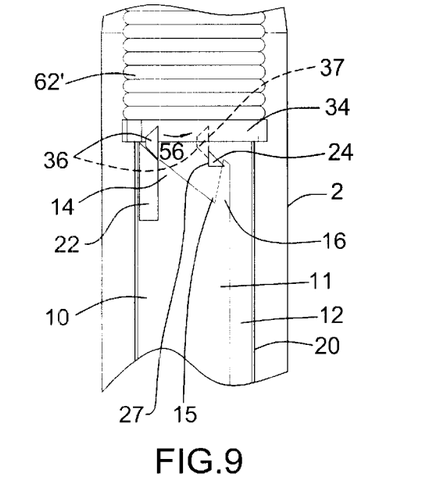
FIG. 9 is a broken longitudinal view in elevation of the portion of the syringe of FIG. 1, wherein the syringe includes an alternative embodiment of the resilient member.

Referring to FIG. 9, a broken view of a syringe near its distal end is illustrated that is substantially similar in design and operation to the syringe described above and illustrated in FIGS. 1 and 6–8. The syringe of FIG. 9 includes a modified resilient member 62' that axially biases ring 34 and vial 20 toward shield proximal end 6 and also rotationally biases the ring in a direction from each first groove 10 toward each second groove 12. The rotational biasing tension of the modified resilient member will result in modified movement of tabs 36 between ridges 14, 16 during operation of the syringe. The movement of each tab 36 within each groove 10 is substantially the same as described above, because the ring is generally prevented from being displaced rotationally within the shield cavity when each tab 36 is received within a corresponding first or second groove 10, 12. However, when the ring and vial are axially displaced an appropriate distance from the shield distal end such that tabs 36 are in position to traverse their corresponding first ridges 14, the rotational biasing tension acting upon ring 34 by modified resilient member 62' will cause immediate rotational displacement of the ring within the shield cavity above ridges 14, 16 upon removal of the applied force to the vial. This rotational displacement causes each tab 36 to traverse a corresponding ridge 14 and move within a corresponding channel 8 toward a corresponding second ridge 16 (depicted by arrow 56 and tab 36 in dashed lines in FIG. 9) rather than sliding along the portion of spline surface 110 located between the corresponding first ridge 14 and valley 15. However, each tab 36 is effectively prevented from immediately traversing corresponding second ridge 16, because a corresponding second protrusion 24 on the vial is appropriately aligned in channel 8 to block access to corresponding second ridge 16 and corresponding second groove 12. Specifically, one side 37 of each tab 36 engages a facing side 27 of the corresponding second protrusion 24.

The rotational biasing tension applied by modified resilient member 62' to ring 34 is typically greater than its axial biasing tension acting on the ring and the vial such that, upon engagement of the facing sides 37, 27 of each tab 36 and each second protrusion 24, the tabs will stay locked with the second protrusions between corresponding first and second ridges 14, 16. This locking arrangement further causes the vial to rotate slightly in the direction of the rotational biasing tension applied by the modified resilient member such that each first protrusion 22 engages an inner sidewall of its corresponding first groove 10 (i.e., a side of raised portion 11 that is adjacent the first groove) and frictionally resists the axial biasing tension of the modified resilient member. Thus, the locking arrangement effectively prevents the ring and vial from being axially displaced toward the shield proximal end and the tabs from being received in their corresponding valleys until an appropriate force is applied to the vial. An example of an appropriate force would be a pull of the plunger away from the vial to aspirate fluid into the vial cavity. The applied force to the vial will cause tabs 36 and second protrusions 24 to move together toward the shield proximal end, thus preventing rotational displacement of the ring, until each tab 36 is received in its corresponding valley 15. When the tabs are completely received in their corresponding valleys, the ring is effectively prevented from further axial or rotational displacement within the shield cavity. The vial will continue to be axially displaced toward the shield proximal end until its flange 30 at its distal end abuts the distal end of the ring. The additional displacement of the vial allows each second protrusion 24 to travel beyond its corresponding tab such that the engaging surfaces 28, 38 of the second protrusions and the tabs are aligned and face each other (i.e., similar to the tab and protrusion positions depicted in FIG. 7). Application of an appropriate force to the vial (e.g., during the release of fluid from the vial cavity by plunger 50) displacing the vial and ring toward the shield distal end will cause second protrusions 24 to engage their corresponding tabs 36 via their complimentary engaging surfaces 28, 38, thus releasing tabs 36 from their corresponding valleys 15. Upon removal of the force applied to the vial, the rotational and axial biasing tension applied to ring 34 by resilient member 62' combined with the camming action between tabs 36 and second protrusions 24 forces the tabs to traverse their corresponding second ridges 16 and appropriately align with their corresponding second grooves 12. When proper alignment of the tabs with the second grooves is achieved, axial displacement of the vial and ring toward the shield proximal end and retraction of the needle to the second retracted position occurs automatically by action of the modified resilient member.

Figure 10:
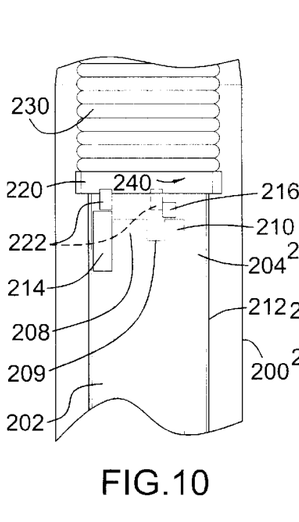
FIG. 10 is a broken longitudinal view in elevation of a portion of an alternative embodiment of the syringe of the present invention near its distal end, wherein the vial and ring are extended within the shield.
Figure 11:
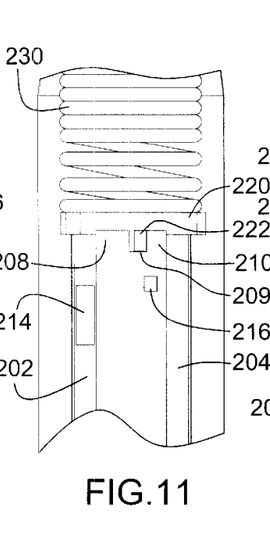
FIG. 11 is a broken longitudinal view in elevation of the portion of the syringe of FIG. 9, wherein the syringe is in a temporary locked position.
Figure 12:
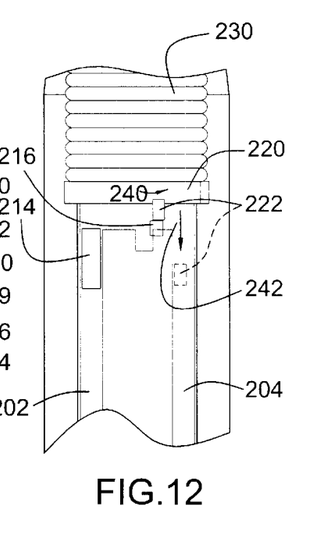
FIG. 12 is a broken longitudinal view in elevation of the portion of the syringe of FIG. 9, wherein the vial and ring are retracting within the shield.

A further embodiment of the syringe of the present invention is illustrated in FIGS. 10–12. This syringe is substantially similar in design and operation to the syringes described above and illustrated in FIGS. 1 and 6–9. However, the protrusions on the vial, the tabs on the ring, the ridges and valleys on the shield and the resilient member have all been modified as described below. Specifically, shield 200 includes a pair of channels substantially similar to the channels described above, wherein each channel includes a first longitudinally extending groove 202, a second longitudinally extending groove 204 separated by a raised portion 201 of the shield interior surface. The first and second grooves communicate at their distal ends via a portion of the channel extending circumferentially along the shield interior surface beyond the distal end of raised portion 201. The distal end of each raised portion is defined by a surface including a rectangular first ridge 208 adjacent the first groove, a rectangular second ridge 210 adjacent the second groove, and a rectangular cut-out portion between the first and second ridges that forms a valley 209. Vial 212 includes a pair of rectangularly shaped first protrusions 214 and a pair of rectangularly shaped second protrusions 216 protruding from the exterior surface of the vial near its distal end. The first protrusions are circumferentially spaced from each other along the exterior surface of the vial, and each second protrusion 216 is spaced an appropriate distance from a respective first protrusion 214. Ring 220, which is disposed between a flange (not shown) at the vial distal end and the first and second protrusions, includes a pair of rectangularly shaped tabs 222 protruding from the exterior surface of the ring and extending beyond its proximal end. The tabs are circumferentially spaced from each other so as to align with a corresponding set of first and second protrusions on the vial and a corresponding channel on the shield interior surface. Additionally, each tab 222 is appropriately dimensioned to be completely received and held within a corresponding valley 209 between corresponding first and second ridges 208, 210. A resilient member 230 is disposed in the shield cavity between the distal end of the shield and the ring. The resilient member biases the ring in both an axial direction toward the proximal end of the shield as well as a rotational direction from first grooves 202 to second grooves 204. It is noted that the rectangular shaped protrusions, tabs, ridges and valleys are merely exemplary, and any geometric shape may be utilized that facilitates operation of the syringe as described below.

In operation, vial 212 and ring 220 are axially displaced toward the shield distal end, thus exposing the needle outside of the shield cavity, by application of an appropriate force to the vial in a substantially similar manner as described above (i.e., the user applies force at a plunger flange and/or a vial flange located at or near the proximal end of the vial). The axial displacement of the vial forces engagement of first protrusions 214 with their corresponding tabs 222, resulting in movement of the first protrusions and tabs in corresponding first grooves 202 toward corresponding first ridges 208. When the tabs are at the distal ends of the first grooves and in position to traverse the first ridges and the applied force to the vial is removed, the rotational biasing tension of resilient member 230 forces ring 220 to rotate in a direction from first grooves 202 to second grooves 204 (depicted by arrow 240 in FIG. 10). It is noted that, due to the rotational biasing tension of the resilient member, no camming action between engaging surfaces of the first protrusions and the tabs is required to facilitate rotational displacement of the ring. The rotation of the ring causes tabs 222 to traverse their corresponding first ridges 208 and travel toward their corresponding second ridges 210. However, each tab 222 is effectively prevented from immediately traversing a corresponding second ridge 210, because a corresponding second protrusion 216 on the vial is appropriately aligned in the corresponding channel to block access to second ridge 210 and second groove 204. Thus, the tabs engage and lock with their corresponding second protrusions (depicted as tab 222 in dashed lines abutting second protrusion 216 in FIG. 10). The rotational biasing tension of the resilient member is typically greater than its axial biasing tension, such that the locking arrangement between the tabs and second protrusions suspends movement of the vial and ring within the shield in a substantially similar manner as described above for the syringe illustrated in FIG. 9. An appropriate force applied to the vial in the direction of the vial proximal end (e.g., caused by a pull of the plunger to aspirate fluid into the vial cavity) forces the vial and ring toward the shield proximal end until tabs 222 are completely received in corresponding valleys 209 and second protrusions 216 are appropriately aligned between the tabs and the shield proximal end (FIG. 11). At the point of disengagement between each tab 222 and its corresponding second protrusion 216, the rotational biasing tension of the resilient member will typically force each tab 222 against a side of a corresponding second ridge 210 adjacent valley 209.

Each tab 222 is released from its corresponding valley 209 upon application of an appropriate force to vial 212 (e.g., a push of the plunger into the vial to fully expel fluid from the vial and needle) that overcomes the axial biasing tension of resilient member 230 applied to the ring and vial. As the vial moves axially within the shield toward the shield distal end, each second protrusion 216 engages corresponding tab 222 (FIG. 12) causing the ring to move axially with the vial. Removal of the applied force to the vial when each tab 222 is in position to traverse its corresponding second ridge 210 results in rotation of the ring by the resilient member (depicted by arrow 240 in FIG. 12). Consequently, tabs 222 traverse their corresponding second ridges 210 and enter corresponding second grooves 202. The axial biasing tension of the resilient member subsequently acts upon ring 220 and vial 212, forcing both toward the shield proximal end and causing tabs 222 to travel accordingly in their corresponding second grooves 202 (depicted by arrow 242 and tab 222 in dashed lines in FIG. 12).

Figure 13:
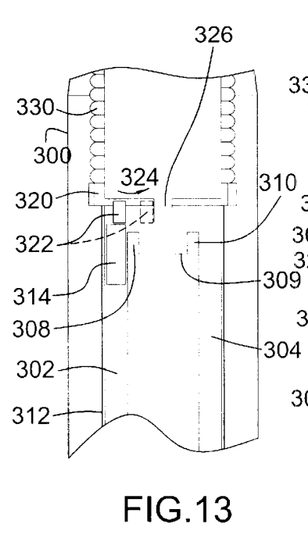
FIG. 13 is a broken longitudinal view in elevation of a portion of a further alternative embodiment of the syringe of the present invention near its distal end, wherein the vial and ring are extended within the shield.
Figures 14, 15:
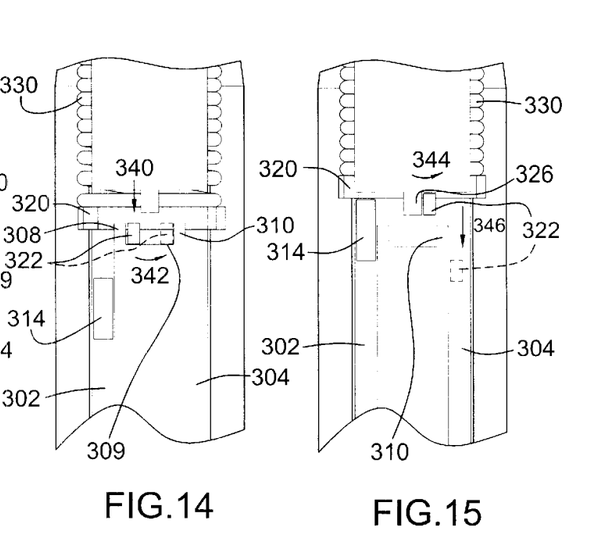
FIG. 14 is a broken longitudinal view in elevation of the portion of the syringe of FIG. 12, wherein the syringe is in a temporary locked position.
FIG. 15 is a broken longitudinal view in elevation of the portion of the syringe of FIG. 12, wherein the vial and ring are retracting within the shield.

Yet another embodiment of the syringe of the present invention is illustrated in FIGS. 13–15. This syringe is substantially similar in design and operation to the syringe described above and illustrated in FIGS. 10–12 but includes certain modifications as described below. Shield 300 of the syringe includes two longitudinally extending channels similar to the channels described above, wherein each channel includes first and second grooves 302, 304 and a raised portion 301 disposed therebetween. A portion of each channel extends circumferentially around the distal end of the raised portion and communicates with the distal ends of the first and second grooves. The distal end of each raised portion includes a surface having a first ridge 308 adjacent the distal end of first groove 302, a second ridge 310 adjacent the distal end of second groove 304 and a valley 309 disposed between the first and second ridges. Each of the ridges and valleys have a rectangular configuration. The shield further includes a pair of second raised portions 325 disposed on the shield interior surface, wherein each second raised portion 325 has an edge that defines a sidewall of a respective channel portion extending around raised portion 301. Each second raised portion 325 includes a rectangular barrier 326 extending from the second raised portion edge and into its respective channel portion. Each barrier 326 is further dimensioned and disposed along the second raised portion edge so as to be aligned an appropriate distance from each of its respective first and second ridges 308, 310 and separated an appropriate distance from its respective valley 309.

The vial utilized in the syringe of FIGS. 13–15 only has a single pair of protrusions. Specifically, vial 312 includes a pair of circumferentially spaced protrusions 314 located near its distal end, wherein each protrusion 314 has a rectangular configuration. Ring 320, which is disposed between a flange (not shown) at the vial distal end and the vial protrusions, includes a pair of rectangularly shaped tabs 322 protruding from the exterior surface of the ring and extending beyond its proximal end. The tabs are circumferentially spaced from each other so as to align with the vial protrusions and the channels on the shield interior surface. Additionally, each tab 322 is appropriately dimensioned for travel around a barrier 326 disposed in a corresponding channel as well as for being received within a corresponding valley 309 between corresponding first and second ridges 308, 310. A resilient member 330 is disposed in the syringe between the distal end of the shield and the ring. The resilient member biases the ring in both an axial direction toward the proximal end of the shield as well as a rotational direction from first grooves 302 to second grooves 304. It is noted that the rectangular shaped protrusions, tabs, barriers, ridges and valleys are merely exemplary, and any geometric shape may be utilized that facilitates operation of the syringe as described below.

In operation, vial 312 and ring 320 are axially displaced toward the shield distal end, thus exposing the needle outside of the shield cavity, by application of an appropriate force to the vial in a substantially similar manner as described above (i.e., the user applies force at a plunger flange and/or a vial flange located at or near the proximal end of the vial). The axial displacement of the vial forces protrusions 314 to engage with their corresponding tabs 322, resulting in movement of the protrusions and tabs in corresponding first grooves 302 toward corresponding first ridges 308. Upon removal of the applied force to the vial when the tabs are positioned at the distal ends of the first grooves and are ready to traverse the first ridges, the rotational biasing tension of resilient member 330 forces ring 320 to rotate in a direction from first grooves 302 to second grooves 304 (depicted by arrow 324 in FIG. 13). The rotation of the ring causes tabs 322 to traverse their corresponding first ridges 308 and travel toward their corresponding second ridges 310. However, each tab 322 is effectively prevented from immediately traversing a corresponding second ridge 310, because a corresponding barrier 326 disposed in the channel blocks access to the corresponding second ridge 310 and second groove 304. Thus, the tabs engage with their corresponding barriers (depicted as tab 322 in dashed lines abutting barrier 326 in FIG. 13).

The rotational biasing tension of resilient member 330 is typically greater than its axial biasing tension, such that the locking arrangement between the tabs and barriers suspends movement of the vial and ring within the shield in a substantially similar manner as described above for the syringes illustrated in FIGS. 9–12. An appropriate force applied to the vial in the direction of the vial proximal end (e.g., caused by a pull of the plunger to aspirate fluid into the vial cavity) forces the vial and ring toward the shield proximal end until tabs 322 disengage from their corresponding barriers 326 and are received in their corresponding valleys 309. Specifically, each tab 322 moves within the channel along an adjacent side of a corresponding barrier 326 (depicted by arrow 340 in FIG. 14) toward a corresponding valley 309 as the ring and vial are withdrawn from the shield proximal end. Upon disengagement of the tabs with the barriers, the ring is immediately rotated within the shield due to the rotational biasing tension applied by the resilient member. The ring and vial may also continue to be axially displaced toward the shield proximal end until the tabs are completely received in their corresponding valleys. The rotation of the ring causes tabs 322 to move within their corresponding valleys 309 toward corresponding second ridges 310 until each tab engages an adjacent side of its second ridge and is beyond the barrier within the corresponding channel (depicted by arrow 342 and tab 322 shown in dashed lines in FIG. 14). When the tabs engage the adjacent sides of their corresponding second ridges, the ring and vial are locked in position within the shield. It is noted that the tabs, ridges, valleys and barriers are all typically dimensioned such that each tab is appropriately displaced within a corresponding valley and incapable of traversing a corresponding second ridge immediately after disengaging with a corresponding barrier. It is further noted that the axial and rotational biasing tension applied by the resilient member may be modified to facilitate automatic travel of the tabs within corresponding channels to a locking position in corresponding valleys when the tabs traverse corresponding first ridges.

Tab 322 is released from valley 309 upon application of an appropriate force to vial 312 (e.g., a push of the plunger into the vial to fully expel fluid from the vial and needle) that overcomes the axial biasing tension of resilient member 330 applied to the ring and vial. As the vial moves axially within the shield toward the shield distal end, each protrusion 314 on the vial engages ring 320 (FIG. 15) causing the ring to move axially with the vial. Removal of the applied force to the vial when each tab 322 is in position to traverse its corresponding second ridge 310 results in rotation of the ring by the resilient member (depicted by arrow 344 in FIG. 15). Consequently, tabs 322 traverse their corresponding second ridges 310 and enter corresponding second grooves 304. The axial biasing tension of the resilient member subsequently acts upon ring 320 and vial 312, forcing both toward the shield proximal end and causing tabs 322 to travel accordingly in their corresponding second grooves 304 (depicted by arrow 346 and tab 322 in dashed lines in FIG. 15).

It will be appreciated that the safety syringe device of the present invention may be implemented in many ways in addition to the exemplary embodiments described above and illustrated in the drawings.

The shield and shield cavity may have any geometric configuration and be constructed of any material suitable for facilitating operation of the device. The shield may further include any number of channels (e.g., one channel) disposed at any location around the circumference of the interior of the shield. The channels may extend any distance along the length of the shield. The ridges and valleys of each channel may have any geometric configuration suitable for facilitating operation of the device. Similarly, the shield may employ any number of barriers corresponding to the number of channels, and each barrier may have any geometric configuration suitable for facilitating operation of the device. Any number of flanges may be disposed on the shield at any suitable location.

The vial may have any geometric configuration and may be constructed of any material suitable for facilitating operation of the device. Any number of first and second protrusions (e.g., one first protrusion and one second protrusion) corresponding to the number of channels on the shield may be disposed on the exterior surface of the vial at any suitable location. Alternatively, the vial may include a single protrusion per shield channel. The protrusions may be of any geometric configuration suitable for operation of the device. Any number of vial flanges may be disposed at any suitable locations along the vial. The vial distal end may be configured to attach to a vacuum needle assembly in any suitable manner (e.g., threaded attachment, frictional fit, etc.).

The ring may be constructed of any suitable material and include any number of tabs (e.g., a single tab) disposed at any location along its outer surface. The tabs may have any geometric configuration suitable for operation of the device. The resilient member may also be constructed of any suitable material and have any configuration suitable for operation of the device. A rotational biasing tension may be loaded into the resilient member during assembly of the device or incorporated into the design of the resilient member, and the rotational biasing tension may be varied to any suitable degree with respect to the axial biasing tension of the resilient member. The resilient sealing member may have any geometric configuration suitable for operation of the device and may be constructed of any material suitable for operation of the device.

From the foregoing description, it will be appreciated that the invention makes available a novel safety syringe device for a single use of a vacuum needle.

Having described preferred embodiments of a new and improved safety syringe device, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A safety syringe for use with a vacuum needle comprising:
   a vial having a proximal end and a distal end configured to attach to said vacuum needle, said vial including at least one first protrusion and at least one second protrusion extending from an exterior surface of said vial, said second protrusion being circumferentially spaced a selected distance from said first protrusion along the vial exterior surface;
   a ring rotatably secured around a portion of said vial between the vial distal end and said protrusions, said ring including at least one tab with an engaging surface projecting from an exterior surface of said ring, wherein the engaging surface of said tab engages with an engaging surface on each of said protrusions during operation of said syringe;
   a shield having an aperture at a proximal end, an aperture at a distal end and a cavity defined therebetween, wherein the shield cavity telescopically receives said vial and said ring at the shield proximal end aperture and the shield distal end aperture permits said vacuum needle attached to the vial distal end to extend from or retract into the shield cavity, and wherein an interior surface of said shield includes at least one channel configured to receive said tab and said first protrusion and permit travel of said tab and said first protrusion between the shield proximal and distal ends;
   a resilient member within the shield cavity to axially bias said vial and said ring within the shield cavity in a direction toward the shield proximal end; and
   a retaining member surrounding a portion of said vial between said protrusions and the vial proximal end, wherein said retaining member is configured to engage and seal the shield proximal end aperture while permitting axial movement of said vial with respect to said retaining member and said shield.

2. The safety syringe of claim 1, wherein said resilient member rotationally biases said ring within the shield cavity.

3. The safety syringe of claim 2, wherein said resilient member is a coil spring.

4. The safety syringe of claim 1, wherein said resilient member comprises a toroidal section and a pair of helical sections extending substantially linearly from said toroidal section at substantially equidistant locations along the circumference of said toroidal section, said helical sections being bendable from at least a substantially coplanar position to at least a substantially perpendicular position with respect to said toroidal section.

5. The safety syringe of claim 1, wherein said vial includes a pair of first protrusions spaced symmetrically on the exterior surface of said vial and a pair of second protrusions spaced symmetrically on the exterior surface of said vial, said ring includes a pair of tabs spaced symmetrically on the exterior surface of said ring and said shield includes a pair of channels spaced symmetrically on the interior surface of said shield.

6. The safety syringe of claim 1, wherein said shield further includes at least one raised portion disposed along the shield interior surface and surrounded by said channel, said raised portion including a distal end defining a first ridge, a second ridge and a valley disposed between said ridges, wherein said ridges face the distal end of said shield and a portion of said channel extends around said ridges.

7. The safety syringe of claim 6, wherein said channel further includes a first groove and a second groove longitudinally aligned along the interior surface of said shield, said first groove is configured to completely receive and provide a travel path for said tab and said first protrusion between the shield proximal end and said first ridge at a distal end of said first groove, and said second groove is configured to completely receive and provide a travel path for said tab between said second ridge at a distal end of said second groove and the shield proximal end.

8. The safety syringe of claim 7, wherein said valley is configured to receive and hold said tab upon traversal of said first ridge by said tab.

9. The safety syringe of claim 8, wherein said first protrusion is aligned on said vial such that, during movement of said first protrusion within said first groove toward the shield distal end, said first protrusion engages said tab at their corresponding engaging surfaces thereby forcing said ring to move axially within said shield and allowing said tab to traverse said first ridge upon displacement of said vial and said ring within said shield a selected distance from the shield proximal end, and said second protrusion is aligned on said vial such that, during movement of said second protrusion toward the shield distal end when said tab is held within said valley, said second protrusion engages said tab at their corresponding engaging surfaces thereby forcing said ring to move axially within said shield and allowing said tab to traverse said second ridge upon displacement of said vial and said ring within said shield the selected distance from the shield proximal end.

10. The safety syringe of claim 9, wherein the engaging surfaces of said tab and said protrusions are configured to engage in a camming relationship such that, upon engagement of said tab with one of said protrusions and displacement of said vial and said ring within said shield the selected distance from the shield proximal end, said tab slides along one of said protrusions and said ring is forced to rotate within said shield in a direction forcing said tab to traverse a corresponding one of said first and second ridges.

11. The safety syringe of claim 9, wherein said resilient member rotationally biases said ring within the shield cavity in a direction from said first groove toward said second groove thereby forcing said tab to traverse said first ridge and said second ridge upon displacement of said vial and said ring the selected distance from the shield proximal end.

12. The safety syringe of claim 11, wherein said second protrusion is further aligned on said vial to prevent traversal of said second ridge by said tab due to rotational displacement of said ring by said resilient member prior to said tab being received and held within said valley.

13. The safety syringe of claim 1, wherein said channel includes at least one sidewall adjacent and non-perpendicular to the shield interior surface.

14. The safety syringe of claim 6, wherein the distal edge of said raised portion is defined by a spline, rotating surface extending between said ridges.

15. The safety syringe of claim 14, wherein a transition angle is defined between said spline, rotating surface and an adjacent wall of the portion of said channel extending around said ridges, and said transition angle varies between about 30° and about 60° at varying positions along said rotating surface.

16. The safety syringe of claim 1, wherein said retaining member is constructed of a acetal resin material.

17. A safety syringe comprising:
   a vial including a protrusion extending from an exterior surface of said vial;

a ring rotatably secured around a portion of said vial between a longitudinal end of said vial and said protrusion, said ring including a tab with an engaging surface projecting from an exterior surface of said ring, wherein the engaging surface of said tab engages with an engaging surface of said protrusion during operation of said syringe; and a shield including a cavity to telescopically receive said vial and said ring, wherein an interior surface of said shield includes a channel configured to receive said tab and permit travel of said tab within the shield cavity, wherein said channel includes a sidewall adjacent and non-perpendicular to the shield interior surface.

18. A safety syringe comprising:

a vial including a protrusion extending from an exterior surface of said vial;

a ring rotatably secured around a portion of said vial and including a tab with an engaging surface projecting from an exterior surface of said ring, wherein the engaging surface of said tab engages with an engaging surface of said protrusion during operation of said syringe;

a shield inclding an aperture at a longitudinal end of said shield and a cavity to telescopically receive said vial and said ring at the shield aperture, wherein an interior surface of said shield includes a channel configured to receive said tab and permit travel of said tab within the shield cavity;

a resilient member within the shield cavity to axially bias said vial and said ring within the shield cavity in a direction away from the shield aperture; and a retaining member surrounding a portion of said vial and configured to engage and seal the shield aperture while permitting axial movement of said vial with respect to said retaining member and said shield.

* * * * *